United States Patent [19]
Cheng

[11] Patent Number: 6,094,152
[45] Date of Patent: Jul. 25, 2000

[54] ALGORITHM FOR A/D WINDOW CONTROL FOR ELECTRONIC PORTAL IMAGE ACQUISITION IN A RADIOTHERAPY SYSTEM

[75] Inventor: Francis T. Cheng, Palo Alto, Calif.

[73] Assignee: Siemens Medical Systems, Inc., Iselin, N.J.

[21] Appl. No.: 09/220,872

[22] Filed: Dec. 23, 1998

[51] Int. Cl.$^7$ .................................................. H03M 1/00
[52] U.S. Cl. ............................................. 341/132; 378/62
[58] Field of Search .................................. 341/132, 139, 341/155; 378/53, 62

[56] References Cited

U.S. PATENT DOCUMENTS

| | | | |
|---|---|---|---|
| 4,264,898 | 4/1981 | Barman et al. | 341/139 |
| 4,383,247 | 5/1983 | Assard | 341/139 |
| 5,296,856 | 3/1994 | Mantong | 341/139 |
| 5,684,850 | 11/1997 | Warburton et al. | 378/53 |

*Primary Examiner*—Trong Phan

[57] ABSTRACT

A robust histogram analysis algorithm is used in accordance with the present invention to control the electronic portal image analog to digital (A/D) window such that the acquired images will have sufficient contrast for their uses in radiotherapy. The algorithm includes setting an initial estimate of a region of interest within a histogram, the histogram including pixel counts and pixel values related to the pixel counts, and determining two dominant peaks inside the region of interest. One of the two dominant peaks is below a predetermined value and the other of the two dominant peaks is between the predetermined value and a second predetermined value. If the one dominant peak is more than two times the standard deviation of the other dominant peak, then a first local minimum to the right of the one dominant peak will be the revised boundary. If the other dominant peak is more than two times the standard deviation of the one dominant peak, then a first local minimum to the left of the other dominant peak will be the revised boundary. Otherwise the average value of the two dominant peaks will be the revised boundary. The algorithm also includes counting the number of pixels outside the revised boundary and determining a mean pixel value outside the revised boundary based upon the pixel count. Furthermore, the algorithm includes accumulating pixel counts in one direction until a predetermined percentage of the pixel counts outside revised estimate of dark region is reached to determine the lower cutoff and accumulating pixel counts in an opposite direction until a predetermined percentage is reached to determine the upper cutoff. Finally, the algorithm includes utilizing the upper and lower cutoffs to set the A/D window.

16 Claims, 11 Drawing Sheets

ALGORITHM FOR A/D WINDOW CONTROL FOR ELECTRONIC PORTAL IMAGE ACQUISITION IN A RADIOTHERAPY SYSTEM

FIELD OF THE INVENTION

The present invention relates generally to electronic image portal image (EPI) acquisition and more particularly to an algorithm for analog to digital window control for such image acquisition.

BACKGROUND OF THE INVENTION

Radiation-emitting devices are generally known and used for radiation therapy in the treatment of patients with cancers. Typically, a radiation therapy device includes a gantry which can be swiveled around a horizontal axis of rotation in the course of a therapeutic treatment. A linear accelerator is located in the gantry for generating a high-energy beam beam for therapy. This high radiation beam can be an electron radiation or photon (X-ray) beam. During treatment, the radiation beam is provided on one zone of a patient lying at the isocenter of gantry rotation.

The goal of radiation treatment planning is to maximize the dose to the target volume while protecting radiation sensitive healthy tissue.

A feature of radiation therapy involves portal images, which are commonly used to verify and record the patient tumor location. Portal images, i.e., images of the port through the patient through which radiation emerges, include manual (film) and electronic images (EPI) taken before, during or after the treatment. Electronic portal images (EPI), when taken before the treatment, give the therapist the opportunity of correcting for minor patient positioning errors. Portal images taken during treatment provide a means of monitoring patient movement. Further, EPI allows therapists to take images remotely without going inside the treatment room.

Because energy of the x-ray for radiotherapy is in thereat megavolt range, images acquired by the traditional film and EPI method in general show lack of details of the patient anatomy. One method of improving EPI image detail contrast is to control the analog to digital (A/D) window of the video capture device so that only part of video signal containing useful image information is digitized.

A conventional system used to control the A/D window has some deficiencies. A conventional method for analyzing the useful information in a particular image comprises constructing a histogram of the area to be imaged and analyzing that area by use of an algorithm. This histogram is plotted with dark pixel values on the left, bright pixels on the right. The analysis comprises determining a sharpest peak point on the left hand side of the histogram to determine the lower cutoff of the image. Typically the lower cutoff is at the nearest local minimum to the right of the sharpest peak. The highest peak on the right hand side of the histogram is then utilized to determine the upper cutoff. Typically the upper cutoff is at the nearest local minimum to the left of the highest peak.

This algorithm functions well with large amount of air and no high contrast objects in the field of view. However, if small amount of air or high contrast objects are in the field of view to the left of the true dark peak, the image of interest may be lost. The algorithm described above also produces dark or white washed images in an unpredictable manner. Finally, this algorithm requires user expertise to manipulate the "gain" and "black level" of the camera. Accordingly, a user can sometimes become frustrated when using the conventional algorithm.

Accordingly, what is needed is a method and system for controlling portal image acquisition and automatically capturing the EPI.

SUMMARY OF THE INVENTION

A robust histogram analysis algorithm is used in accordance with the present invention to control the electronic portal image analog to digital (A/D) window such that the acquired images will have sufficient contrast for their uses in radiotherapy. The algorithm includes setting an initial estimate of the dark region within a histogram, which relates pixel counts and the corresponding pixel values, and determining two dominant peaks inside the dark region. The first of the two dominant peaks is below a predetermined value and the second of the two dominant peaks is between the predetermined value and a second predetermined value.

If the first dominant peak is more than two times the standard deviation of the other dominant peak, then the first local minimum to the right of the one dominant peak will be the revised boundary. If the, second dominant peak is more than two times the standard deviation of the first dominant peak, then the first local minimum to the left of the second dominant peak will be the revised boundary. Otherwise the average value of the two dominant peaks will be the revised boundary.

The algorithm also includes counting the number of pixels outside the revised boundary and determining a mean pixel value outside the revised boundary based upon the pixel count. Furthermore, the algorithm includes accumulating pixel counts in one direction from the mean pixel valve until a predetermined percentage of the pixel counts outside revised estimate of dark region is reached to determine the lower cutoff and accumulating pixel counts in an opposite direction from the mean pixel value until a predetermined percentage is reached to determine the upper cutoff. Finally, the algorithm includes utilizing the upper and lower cutoffs to set the A/D window.

The analysis algorithm is robust, produces good quality images under different imaging conditions: different field sizes, various amounts of air in the field of view, the presence of high contrast objects in the field of view. Under most of the clinical imaging condition, the user only need to adjust the "gain" knob of the camera, while the "black level" knob of the camera is set at a neutral position.

DETAILED DESCRIPTION OF THE INVENTION

The present invention relates to an improvement in electronic portal image acquisition. The following description is presented to enable one of ordinary skill in the art to make and use the invention and is provided in the context of a patent application and its requirements. Various modifications to the preferred embodiment will be readily apparent to those skilled in the art and the generic principles herein may be applied to other embodiments. In the following, the invention is described with primary reference to a system for delivering X-ray radiation to a field on a patient. This is by way of example. Thus, the present invention is not intended to be merely limited to the embodiment shown but is to be accorded the widest scope consistent with the principles and features described herein.

Figure 1:
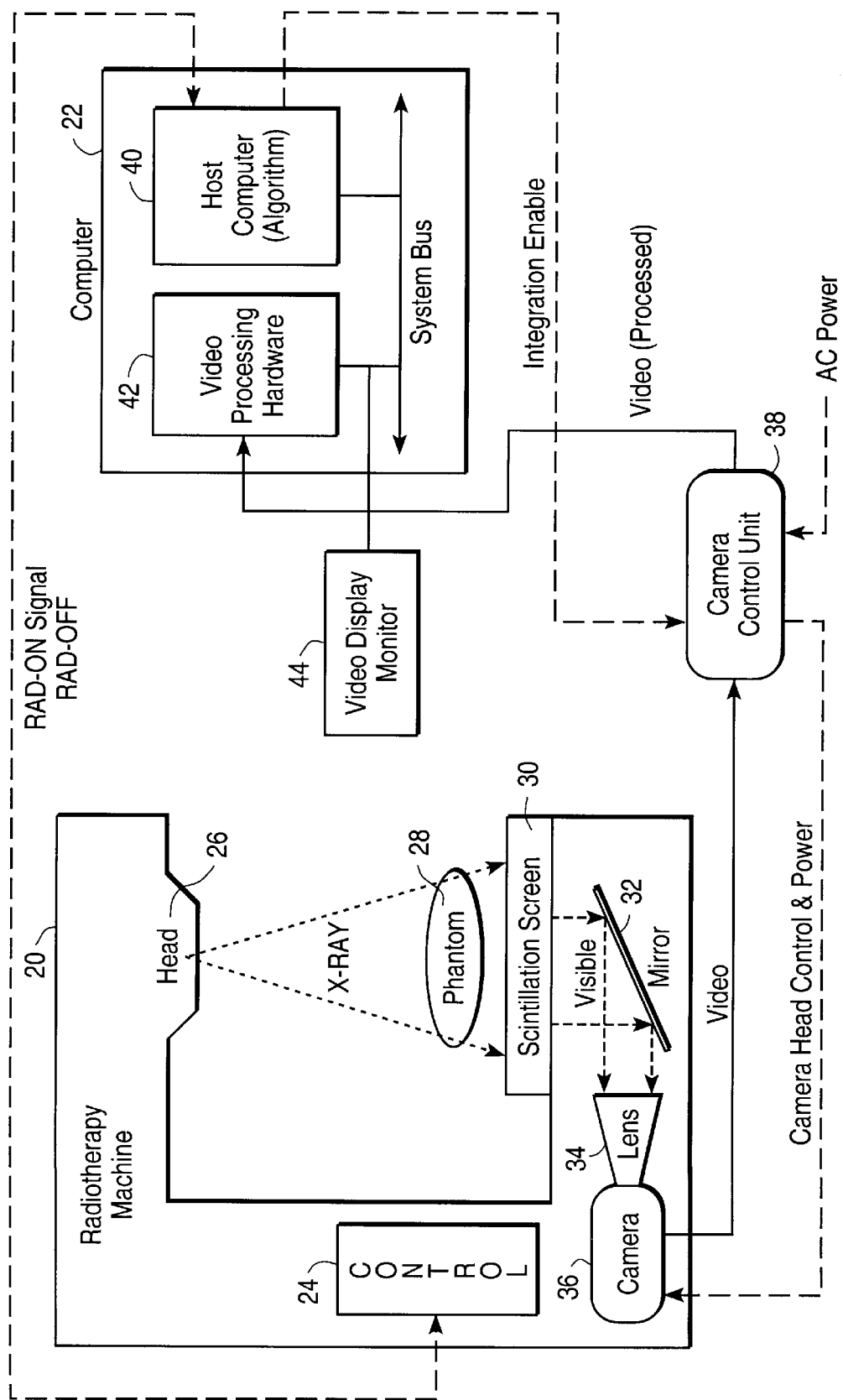
FIG. 1 illustrates a radiotherapy system with an electronic portal imager device with portal imaging control in accordance with the present invention.

FIG. 1 presents an illustrative radiotherapy system including an electronic portal imager device with portal imaging control in accordance with the present invention. The device includes a radiotherapy machine 20 controlled by a computer 22, the computer 22 sending signals to a control unit 24 for turning radiation on or off (RAD-ON or RAD-OFF). The radiation is delivered through a head 26 of the radiotherapy machine 20 to a treatment area 28 of a patient, with delimiting of the field using at least one movable plate/jaw (not shown) in the beam path, if desired. Imaging of the treatment area 28 occurs by way of a scintillation screen 30, i.e., a radiation detector comprising a metal plate and fluorescent screen, that transfers radiation energy of the treatment beam (X-RAY) passing through the treatment area 28 into visible light energy. The visible light is reflected by a mirror 32 to a lens 34 of a camera 36, e.g., a video camera. A camera control unit 38 provides camera head control and power for the camera 36, as is well understood by those skilled in the art. Further, the camera control unit 38 receives control signals from a host computer portion 40 of the computer 22 and provides video image signals for processing by a video processor 42 of the computer 22 in accordance with the present invention. Processed images are suitably displayed via a video display monitor 44.

Figure 2:
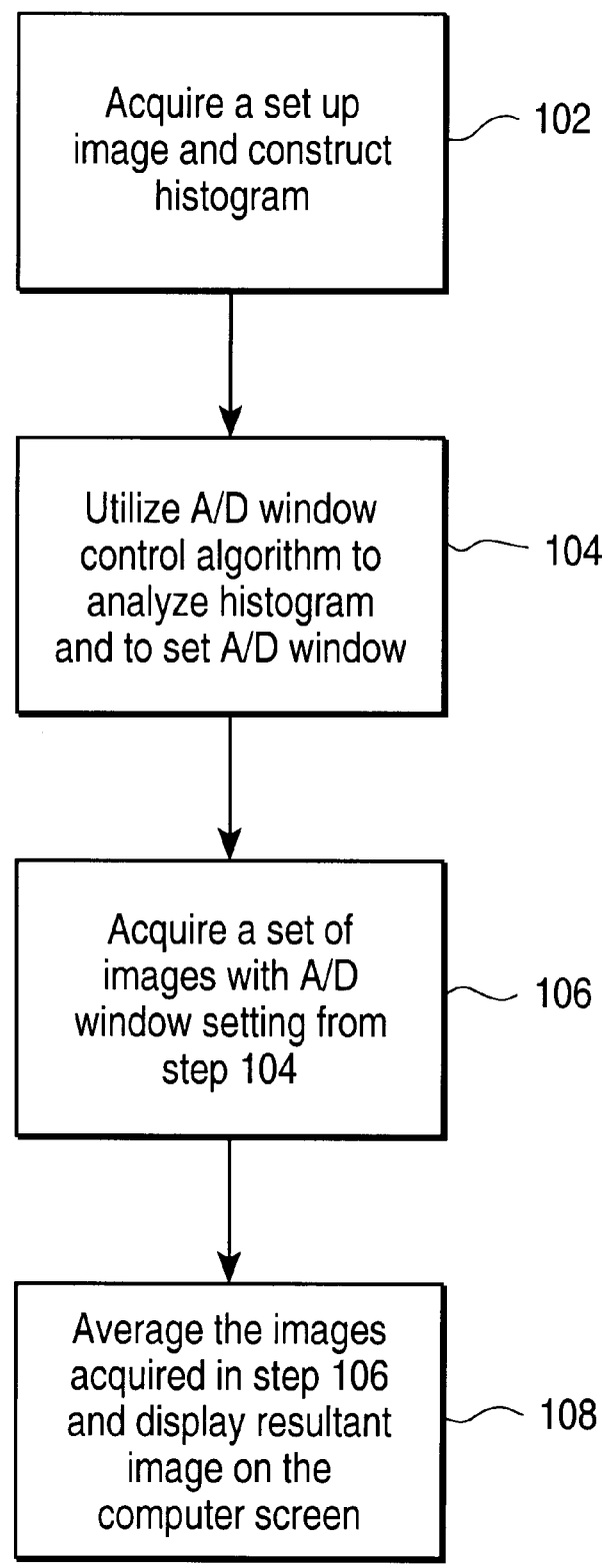
FIG. 2 illustrates a block flow diagram of a process for image capture operation in accordance with a preferred embodiment of the present invention.

An electronic portal image (EPI) acquisition process is utilized in conjunction with the radiotherapy system to acquire the image. The process comprises an algorithm which is executed within the host computer 40 to control an analog to digital (A/D) window within the video processing hardware 42. The EPI acquisition process typically includes four steps which are shown in FIG. 2:

1. Acquire a setup image with the A/D window of the image capture device wide open to digitize the full range of the video signal. A histogram is constructed for analysis. (Step 102)

2. The A/D window control algorithm analyzes the histogram to determine the region of interest and to set the A/D window to digitize the video signal within a subrange of the region of interest. (Step 104)

3. The image acquisition system continues to acquire a set of images with the A/D window setting determined by Step 104 above. (Step 106)

4. The image acquisition system averages the images acquired in step 106 above, and then displays the resultant image on the computer screen. (Step 108)

A conventional A/D window control algorithm performs the analysis step (step 104 above) by detecting the sharpest peak on the left hand side of the histogram to determine a lower cut-off point for the region of interest and uses the highest peak from the right hand side of the histogram to determine the upper cutoff of the histogram.

Figure 3:
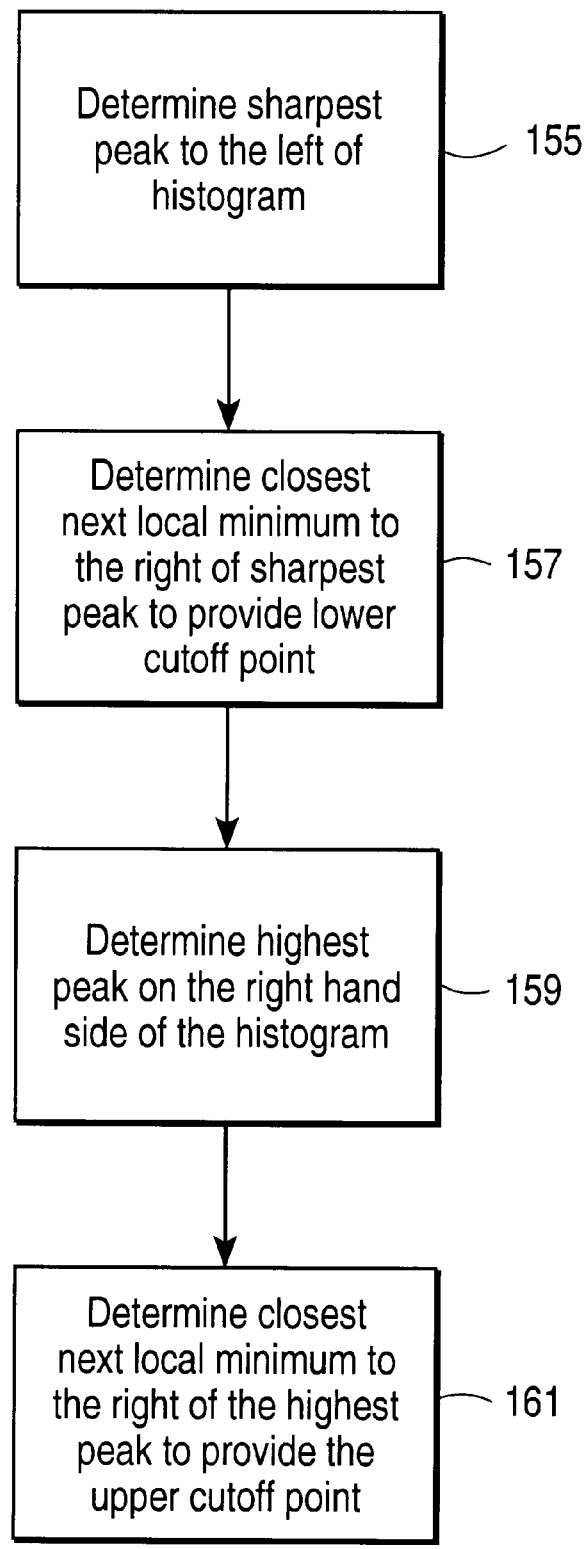
FIG. 3 shows a conventional A/D control algorithm.

The analysis step, step 104, is important to set an accurate region of interest and set the A/D window at a point where all of the information regarding the region of interest is accumulated. Referring now to FIG. 3, what is shown is a flow chart of the conventional algorithm for analyzing a histogram to determine the appropriate region of interest. As is seen first, the sharpest peak to the left of the histogram is determined, via step 155. Then the closest next local minimum to the right of the sharpest peak is determined, via step 157. The local minimum is the point where the region of interest starts or the lower cutoff. Next, the highest peak on the right hand side of the histogram is determined, via step 159. Thereafter, the first local minimum to the left of the highest peak is determined to be the end of the region of interest or the upper cutoff, via step 161.

Figure 4:
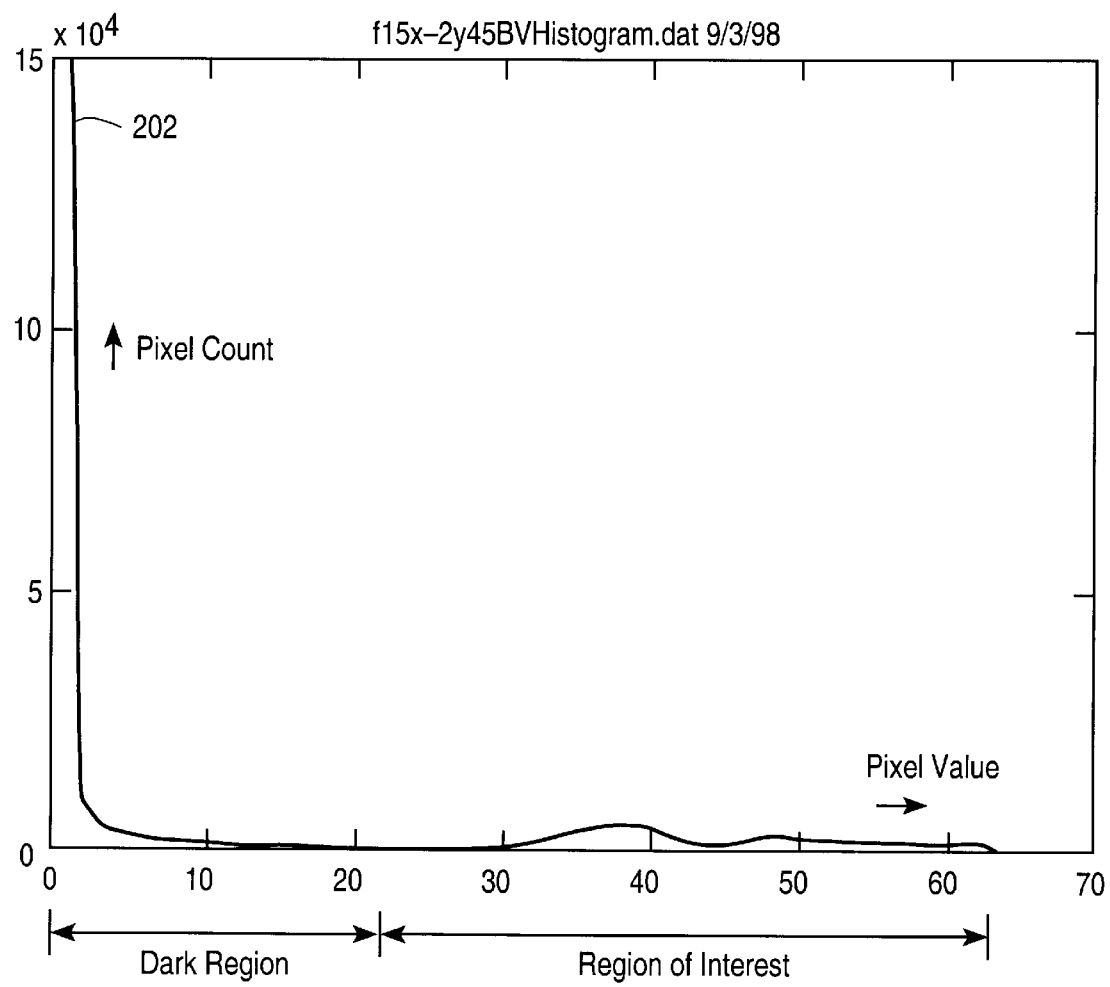
FIG. 4 shows a well behaved sample histogram.

A well-behaved 64-bins histogram is shown in FIG. 4. In this histogram, the ordinant is pixel count and the absciss is the pixel values. Accordingly, for this histogram the maximum pixel count $1.5 \times 10^4$ pixels and the maximum pixel value is 64. In this embodiment 64 pixel value corresponds, for example, to 714 millivolts. The dark region, for example, is, for example, approximately the pixel value of 22 (the region which includes a collimator or the like). The dark region contains pixel values representing the dark areas inside the field of view. Useful patient image information is embedded in the region of interest which is shown outside of the dark region of the histogram. The goal of an A/D window control algorithm is to estimate the dark region and then to pick out a sub-region inside the region of interest for the setting of the A/D window such that most of the patient image information is preserved in the acquired image.

Analyzing the histogram of FIG. 4, in accordance with the conventional algorithm of FIG. 3, the sharpest peak to the left of the histogram is at point 202, then the next local minimum 204 to the right of the sharpest peak is where the region of interest starts. Next, the highest peak on the left hand side of the histogram is determined at 205. The first local minimum to the right of the highest peak is determined at 206. In the histogram shown in FIG. 4, accordingly, it would be possible to obtain most of the relevant region of interest.

Figure 5:
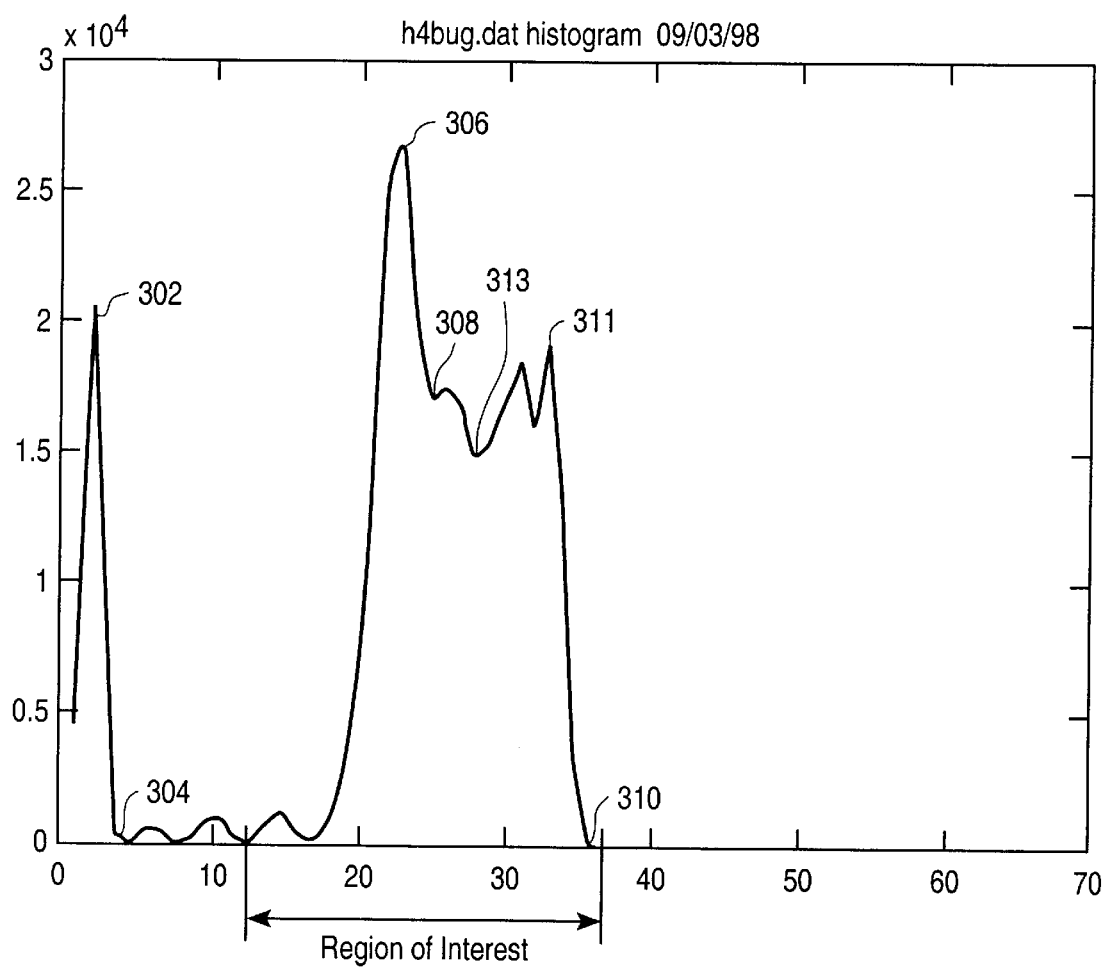
FIG. 5 shows a sample histogram of a scene containing high contrast objects.
Figure 6:
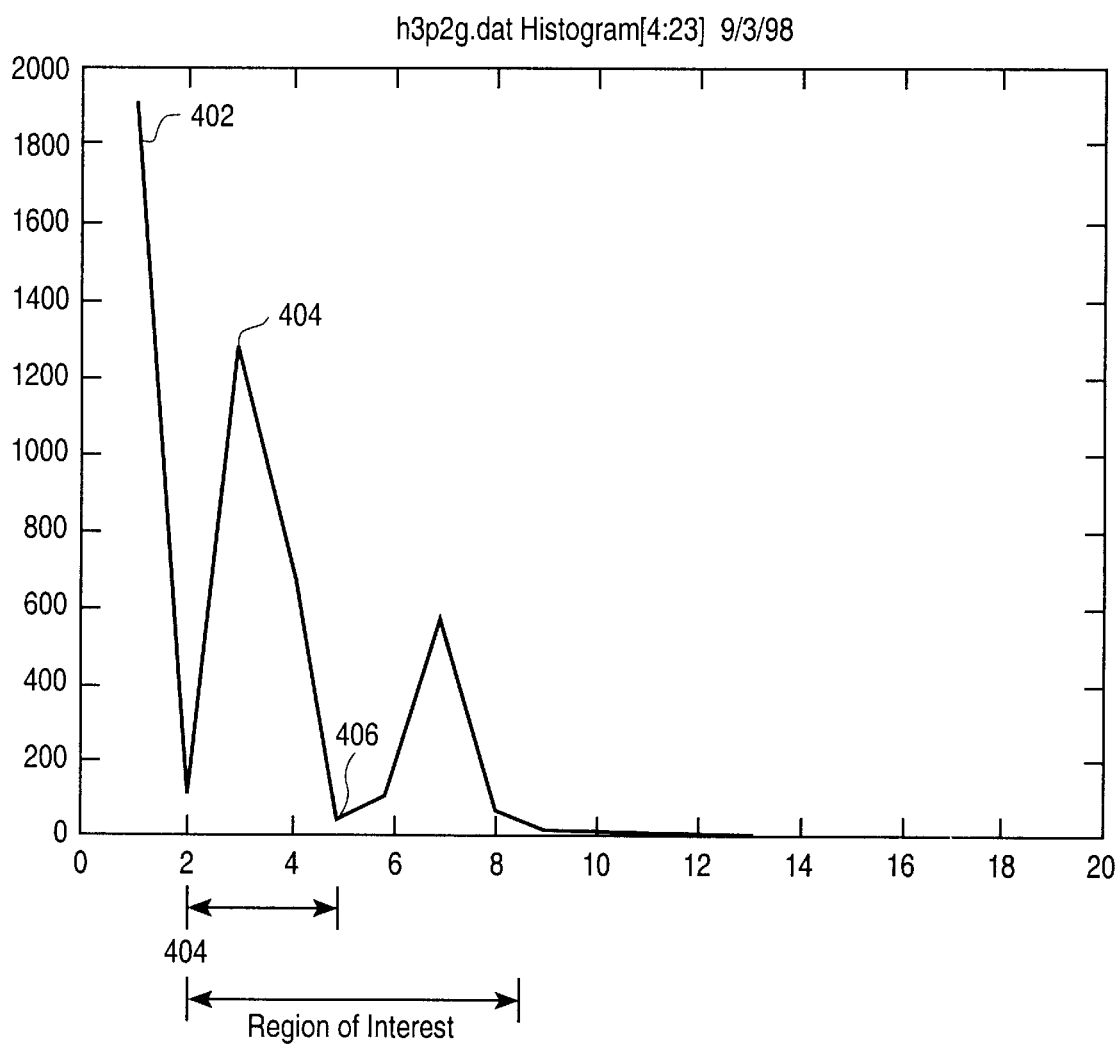
FIG. 6 shows a histogram with air in field manifested as a peak on the right.
Figure 7:
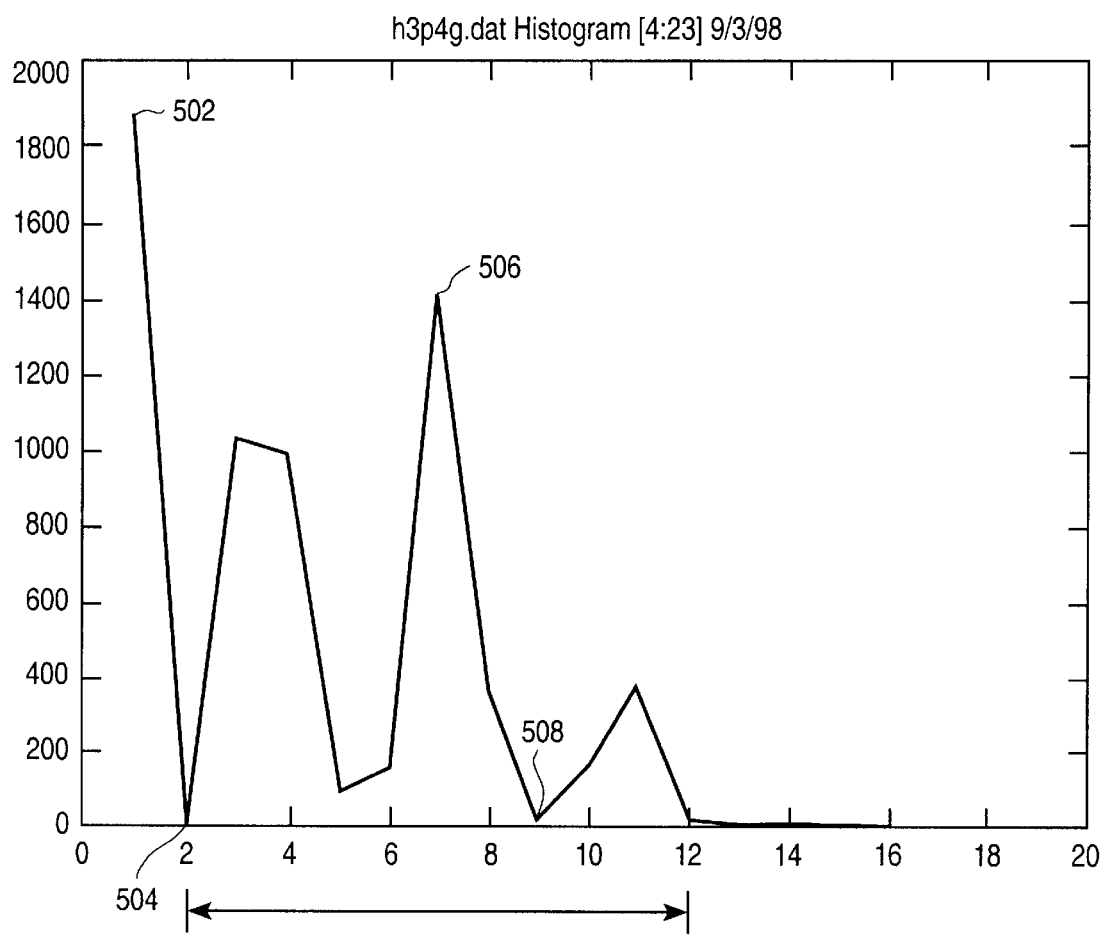
FIG. 7 shows a histogram with complicated structures.
Figure 8:
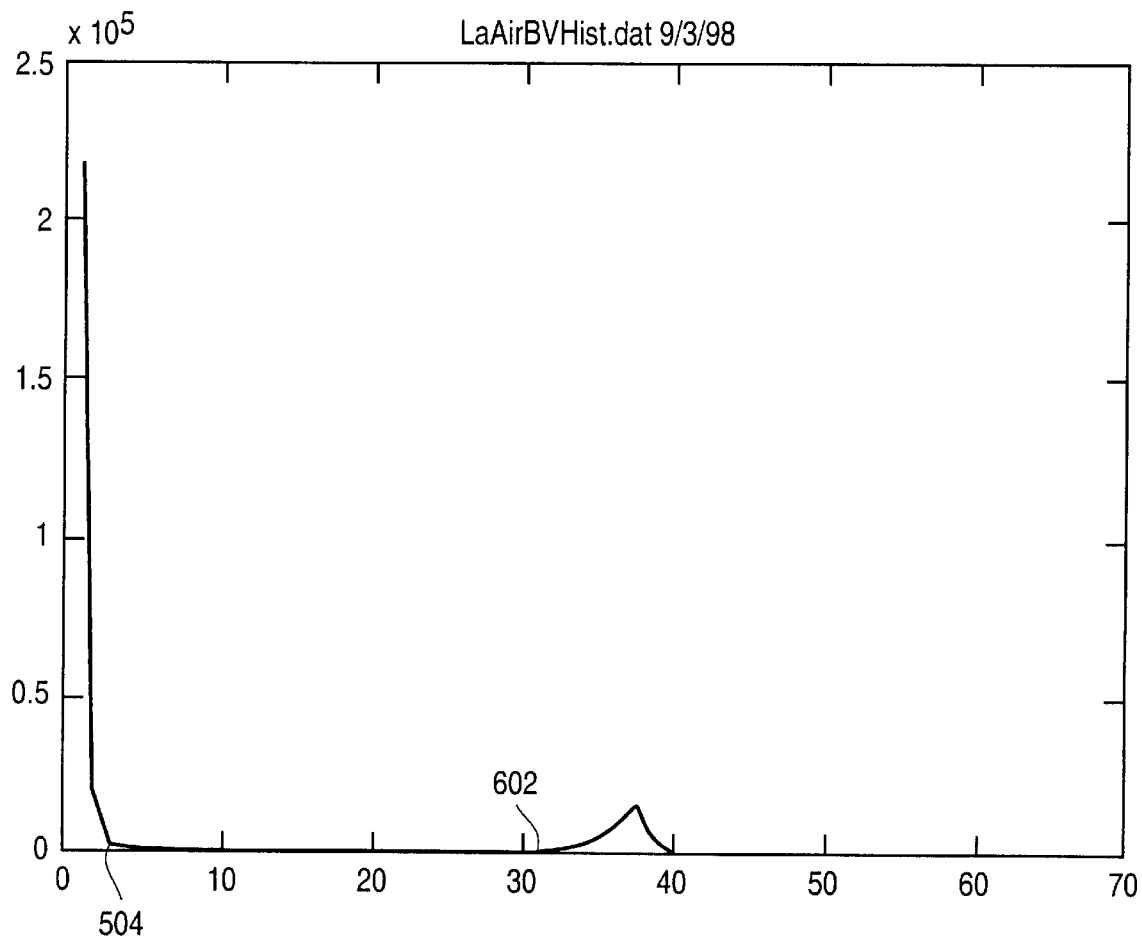
FIG. 8 shows a histogram with image information resides in a small island.

However, the robustness of an A/D window control algorithm is judged by its ability to handle not well behaved histograms. FIG. 5 through FIG. 8 shows examples of these not well behaved histograms. FIG. 5 shows a sample histogram of a scene containing high contrast objects. FIG. 6 shows a histogram with air in field manifested as a peak on the right. FIG. 7 shows a histogram with complicated structures. FIG. 8 shows a histogram with image information residing in a small island.

The conventional algorithm for analyzing a histogram has some deficiencies when analyzing these not well-behaved histograms.

Referring to FIG. 5, which shows a sample histogram of a scene containing high contrast objects, the sharpest peak to the left is at 302. The first local minimum is at 304 which is the lower cutoff. The highest peak on the right hand side would be at point 306. The local minimum to its left would be at 308 which is the upper cutoff. Accordingly, as is seen, much of the information in the region of interest between 308 and 310 is lost.

FIG. 6 shows a histogram with air in the field manifested as a peak on the right. As is seen, the sharpest peak is at 402.

The local minimum is at 404. The highest peak to the left would be 406 and the local minimum is 408. Once again some of the information from the region of interest is lost because there are patient information partially covered under peak 406.

FIG. 7 shows a histogram with complicated structures. The sharpest peak is at 502. Its corresponding local minimum is at 504. The highest peak to the right is at 506. Its corresponding local minimum is at 508. Accordingly, once again much of the region of interest is lost.

FIG. 8 shows a histogram with image information residing in a small island. The sharpest peak is at 602. Its corresponding local minimum is at 604. The highest peak to the right is at 606. Its corresponding local minimum is at 608. Accordingly, once again much of the region of interest is lost.

Accordingly, what is needed is a more robust algorithm that will allow for accurate imaging of the regions of interest. The system should be easily implemented utilizing existing equipment and should not require significant modification thereof. The present invention is directed toward a new algorithm which will handle histograms that are not well behaved, such as those shown in FIGS. 5 through 8. To more clearly understand the operation of the present invention, refer now to the following description in conjunction with the accompanying figure.

Figure 9A:
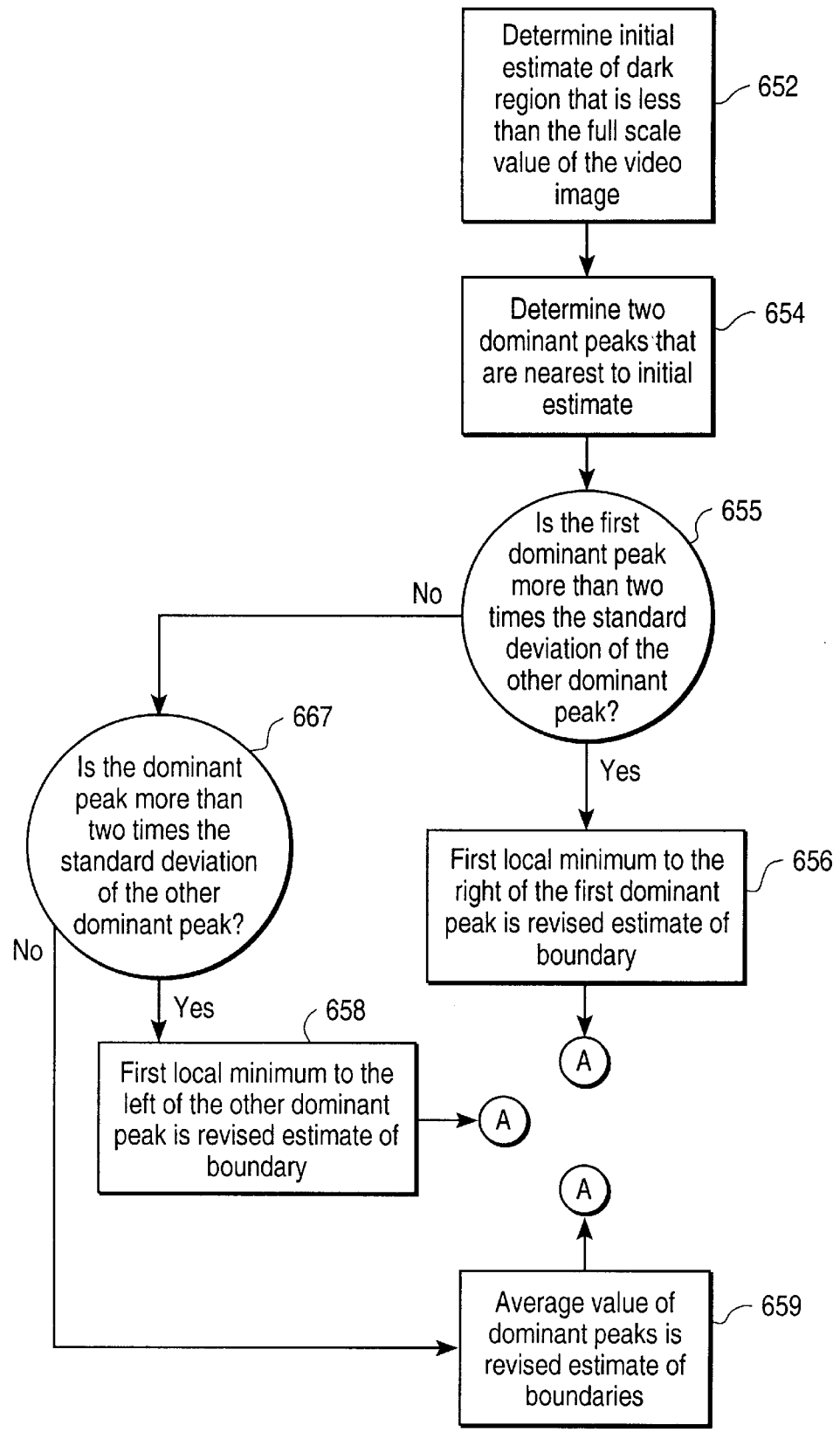
FIG. 9 is a flow diagram of the analysis of a histogram of an image in accordance with the present invention.
Figure 9B:
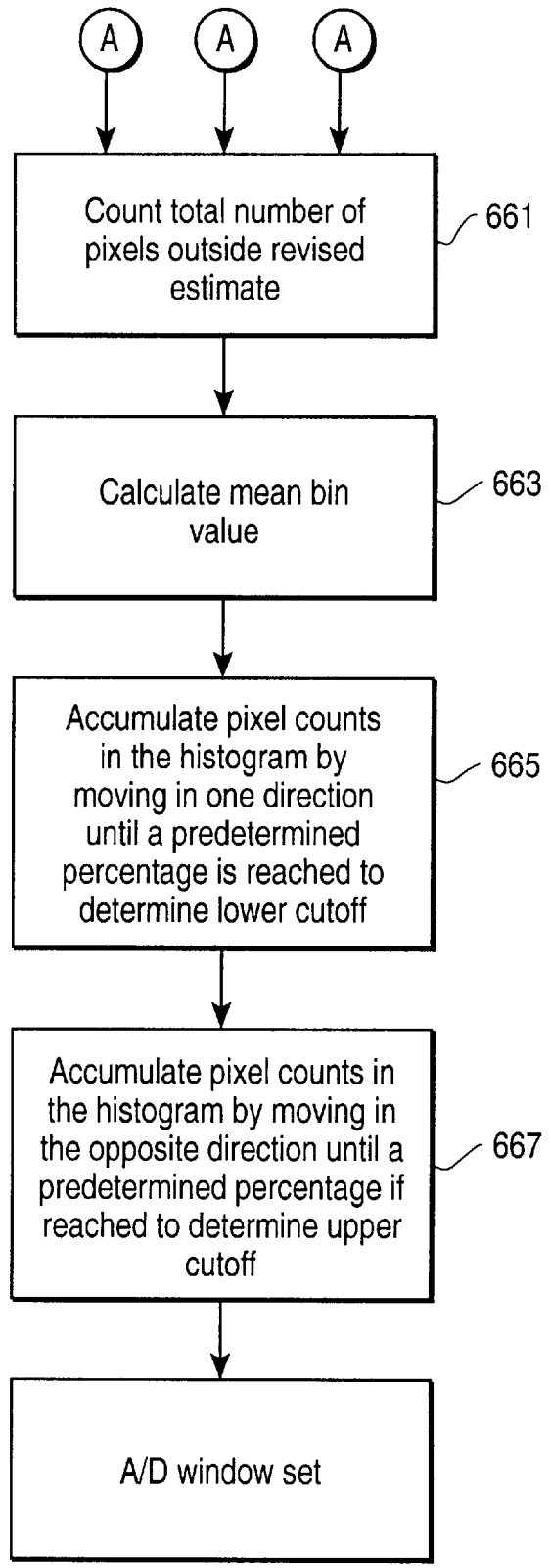

FIG. 9 is a flow diagram of the analysis of a histogram of an image in accordance with the present invention. First, an initial estimate of the dark region is determined that is less than the full scale of the video image, via step 652. Next, the two dominant peaks that are nearest to the initial estimated dark region are determined, via step 654. Next, if the dominant peak of one of the dominant peaks is more than two times the standard deviation of the other dominant peak, via step 655, then the first local minimum to the right of the one dominant peak will be the revised estimate of the boundary of the dark region, via step 656. If the other dominant peak is more than two times the standard deviation of the first dominant peak, via step 657, then the first local minimum to the left of the other dominant peak will be the revised estimate of the boundary of the region, via step 658.

If neither of these conditions are met, the average value of the two dominant peaks will be a revised estimate of the boundary, via step 659. Thereafter, the total number of pixels outside the revised estimate of the boundary are counted, via step 661. Next, the mean bin value of the histogram is calculated based upon the total number of pixels, via step 663. Thereafter, by moving horizontally on the histogram in one direction from the new bin value pixel counts are accumulated in the histogram until a predetermined percentage of the total pixel count outside the revised estimate of the boundary is reached, via step 665. The lowest histogram value is the lower cutoff, and it will be used to set the A/D window lower boundary. Therefore, pixel counts are accumulated by moving horizontally in an opposite horizontal direction in the histogram until the predetermined percentage of the total pixel count outside the revised estimate of the boundary is reached, via step 667. This value will be used to set the upper cutoff and will be used to set the A/D window for the upper boundary.

Through this system, a robust algorithm allows for accurate imaging of the region of interest. To describe this in the context of a specific embodiment, refer to the following.

The detailed steps of the analysis in accordance with the present invention are described hereinbelow.

Step 1. Set the initial estimate of the dark region to be below a predetermined range below the full scale video image (i.e., below 200 millivolt out of the 714 mv full scale). This initial estimate is based on empirical evidence gained by the examination of a large number of portal image histograms acquired under different imaging conditions.

Step 2. Find the two dominant peaks inside the initial estimated dark region: for example, the dominant peak below 100 mv and the dominant peak between 100 mv and 200 mv.

Step 3. If the dominant peak below 100 mv, for example, is more than two times the standard deviation of the dominant peak between 100 mv and 200 mv, then the first local minimum to the right of the dominant peak below 100 mv will be the revised estimate of the boundary of the dark region.

If the dominant peak between 100 mv and 200 mv is more than two times of the standard deviation of the dominant peak below 100 mv, then the first local minimum to the left of the dominant peak between 100 mv and 200 mv will be the revised estimate of the boundary of the dark region.

In all other areas, the average bin value of the two dominant peaks' bin value will be the revised estimate of the boundary of the dark region.

Step 4: Count the total number of pixels outside the revised estimate of the boundary.

Step 5: Find the mean bin value outside the revised estimate of the boundary.

Step 6: From the mean bin value calculated in Step 5, move in the dark region direction and accumulate pixel counts in the histogram bins until a predetermined percentage of the total pixel count outside the revised estimate of the boundary is reached. In a preferred embodiment this predetermined percentage is 47.5%. The lowest histogram bin reached is the lower-cutoff, and it will be used to set the A/D window lower bound.

Step 7: From the mean bin value calculated in Step 5, move opposite from the dark region direction and accumulate pixel counts in the histogram bins until the predetermined percentage of the total pixel count outside the revised estimated dark region is reached. In a preferred embodiment this predetermined percentage is 47.5%. The highest histogram bin reached is the upper-cutoff, and it will be used to set the A/D window upper bound.

Step 8: Convert the lower-cutoff and upper-cutoff bin values to A/D hardware register values, and set the A/D window of the image acquisition hardware.

To illustrate how the algorithm in accordance with the present invention would be used with a not well behaved algorithm, refer now to the following discussion in conjunction with FIG. 5.

First the two dominant peaks are peaks 302 and 306. Since neither of the peaks are twice the standard deviation of the other, then an average of the two peaks (point 313) would be the revised boundary. Thereafter, by moving a predetermined percentage (in a range between 45% to 47.5%) of the pixel count in both directions from the mean pixel value 307, the region of interest can be obtained covering most of the area from 308 to 310. This algorithm can be used advantageously on other not well behaved histograms such as those shown in FIGS. 6–8 to obtain the region of interest in a more effective manner than using conventional algorithms.

A robust histogram analysis algorithm is used to control the electronic portal image analog to digital (A/D) window such that the acquired images will have sufficient contrast for their uses in radiotherapy. The new algorithm is robust, it produces good quality images under different imaging conditions: different field sizes, various amounts of air in the field of view, the presence of high contrast objects in the field of view. Under most of the clinical imaging condition, the user only need to adjust a "gain" knob of the image capture device, while the "black level" knob of the image capture device is set at a neutral position.

Although the present invention has been described in accordance with the embodiments shown, one of ordinary skill in the art will readily recognize that there could be variations to the embodiments and those variations would be within the spirit and scope of the present invention. Accordingly, many modifications may be made by one of ordinary skill in the art without departing from the spirit and scope of the appended claims.

What is claimed is:

1. A system for setting an analog to digital (A/D) window control for image acquisition in a radiotherapy system comprising the steps of:

means for setting an initial estimate of a dark region within a histogram, the histogram including pixel counts and pixel values related to the pixel counts;

means for determining two dominant peaks inside the dark region, one of the two dominant peaks being below a first predetermined value and the other of the two dominant peaks being between the first predetermined value and a second predetermined value, if the one dominant peak is more than two times the standard deviation of the other dominant peak, then a first local minimum to the right of the one dominant peak will be the revised boundary, if the other dominant peak is more than two times the standard deviation of the one dominant peak, then a first local minimum to the left of the other dominant peak will be the revised boundary; otherwise the average value of the two dominant peaks will be the revised boundary;

means for counting the number of pixels outside the revised boundary;

means for determining a mean pixel value outside the revised boundary based upon the pixel count;

means for accumulating pixel counts in one direction from the mean pixel value until a predetermined percentage of the pixel counts outside the revised boundary is reached to determine the lower cutoff value;

means for accumulating pixel counts in an opposite direction form the one direction from the mean pixel value until a predetermined percentage is reached to determine the upper cutoff value; and means for utilizing the upper and lower cutoff values to set the A/D window.

2. The system of claim 1 wherein the first predetermined value in 100 millivolts and the second predetermined value being 200 millivolts.

3. The system of claim 1 in which the predetermined percentage is in the range between 45% and 47.5%.

4. The system of claim 1 in which the histogram includes a plurality of bins.

5. The system of claim 1 wherein the initial estimate is less than a full value of the image.

6. The system of claim 5 wherein the full value of image is 700 millivolts.

7. The system of claim 6 wherein the initial estimate is below 200 millivolts.

8. The system of claim 1 wherein utilizing step (g) further comprises means for converting the upper and lower cutoff values to register values; and means for utilizing the register values to set the A/D window.

9. A method for setting an analog to digital (A/D) window control for image acquisition in a radiotherapy system comprising the steps of:

(a) setting an initial estimate of the dark region within a histogram, which relates pixel counts and the corresponding pixel values;

(b) determining two dominant peaks inside the dark region, the first of the two dominant peaks being below a first predetermined value and the second of the two dominant peaks being between the first predetermined value and a second predetermined value, if the first dominant peak is more than two times the standard deviation of the second dominant peak, then a first local minimum to the right of the first dominant peak will be the revised boundary, if the second dominant peak is more than two times the standard deviation of the first dominant peak, then a first local minimum to the left of the other dominant peak will be the revised boundary; otherwise the average value of the two dominant peaks will be the revised boundary;

(c) counting the number of pixels outside the revised boundary;

(d) determining a mean pixel value outside the revised boundary based upon the pixel count;

(e) accumulating pixel counts in one direction from the mean pixel value until a predetermined percentage of the pixel counts outside the revised boundary is reached to determine the lower cutoff value;

(f) accumulating pixel counts in an opposite direction from the one direction from the mean pixel value until a predetermined percentage is reached to determine the upper cutoff value; and (g) utilizing the upper and lower cutoffs to set the A/D window.

10. The method of claim 9 wherein the first predetermined value in 100 millivolts and the second predetermined value being 200 millivolts.

11. The method of claim 9 in which the predetermined percentage is in the range between 45% and 47.5%.

12. The method of claim 9 in which the histogram includes a plurality of bins.

13. The method of claim 9 wherein the initial estimate is less than a full value of the image.

14. The method of claim 13 wherein the full value of image is 700 millivolts.

15. The method of claim 14 wherein the initial estimate is below 200 millivolts.

16. The method of claim 9 wherein utilizing step (g) further comprises (g1) converting the upper and lower cutoff values to register values; and (g2) utilizing the register values to set the A/D window.

* * * * *